United States Patent [19]
Steiger et al.

[11] Patent Number: 5,159,828
[45] Date of Patent: Nov. 3, 1992

[54] MICROACCUMULATOR FOR MEASUREMENT OF FLUID VOLUME CHANGES UNDER PRESSURE

[75] Inventors: Ronald P. Steiger, Houston; Peter K. Leung, Sugar Land, both of Tex.

[73] Assignee: Exxon Production Research Company, Houston, Tex.

[21] Appl. No.: 577,338

[22] Filed: Aug. 31, 1990

[51] Int. Cl.$^5$ .............................. G01N 15/08
[52] U.S. Cl. .......................................... 73/38
[58] Field of Search .................. 73/3, 38, 149, 864.62

[56] References Cited

U.S. PATENT DOCUMENTS

| | | | |
|---|---|---|---|
| 2,967,427 | 1/1961 | Blanc | 73/149 |
| 3,199,341 | 8/1965 | Heuer, Jr. et al. | 73/820 |
| 3,421,366 | 1/1969 | Ely | 73/819 |
| 3,423,994 | 1/1969 | Scott et al. | 73/819 |
| 3,423,995 | 1/1969 | Scott et al. | 73/819 |
| 3,457,777 | 7/1969 | Nielsen | 73/84 |
| 3,505,860 | 4/1970 | Bishop et al. | 73/819 |
| 3,610,032 | 10/1971 | DiCrispino | 73/819 |
| 3,616,685 | 11/1971 | Strom | 73/819 |
| 3,635,078 | 1/1972 | Wissa | 73/89 |
| 3,728,895 | 4/1973 | Shaw | 73/94 |
| 3,817,109 | 6/1974 | Audet et al. | 73/807 |
| 3,820,385 | 6/1974 | Cordoba | 73/84 |
| 3,881,345 | 5/1975 | Souder | 73/94 |
| 3,975,950 | 8/1976 | Erdei | 73/94 |
| 4,430,890 | 2/1984 | Hains | 73/147 |
| 4,487,056 | 12/1984 | Wiley | 73/38 |
| 4,502,338 | 3/1985 | Smith et al. | 73/819 |
| 4,506,542 | 3/1985 | Rose | 73/38 |
| 4,561,289 | 12/1985 | Jones | 73/38 |
| 4,562,726 | 1/1986 | Barnaby | 73/38 |
| 4,587,857 | 5/1986 | Bush | 73/863 |
| 4,599,891 | 7/1986 | Brauer et al. | 73/38 |
| 4,607,532 | 8/1986 | Arthur et al. | 73/819 |
| 4,627,270 | 12/1986 | Jones | 73/38 |
| 4,631,677 | 12/1986 | Park et al. | 364/422 |
| 4,638,447 | 1/1987 | Odeh | 364/556 |
| 4,643,019 | 2/1987 | Jones | 73/38 |
| 4,648,261 | 3/1987 | Thompson et al. | 73/38 |
| 4,649,737 | 3/1987 | Jones | 73/38 |
| 4,669,299 | 6/1987 | Closmann | 73/38 |
| 4,679,421 | 7/1987 | Barree | 73/38 |
| 4,679,441 | 7/1987 | Johnson et al. | 73/798 |
| 4,710,948 | 12/1987 | Withjack | 378/208 |
| 4,715,212 | 12/1987 | Johanson | 73/38 |
| 4,733,568 | 3/1988 | Koopmans et al. | 73/784 |
| 4,753,107 | 6/1988 | Reed et al. | 73/38 |

(List continued on next page.)

OTHER PUBLICATIONS

"Drilling Fluids", Exxon Production Research Company, 1989.
"The Mechanics of Soils", Atkinson et al., 1978, pp. 118-144, 184-209, 292-343.
"Soil Mechanics", Lambe et al., 1969, Chapter 20, pp.295-303.
"Quantitative Determination of the Mechanical Properites of Shales", Steiger and Leung, SPE Conference, Oct. 2-5, 1988.
"Predictions of Wellbore Stability in Shale Formations At Great Depth", Steiger and Leung, SPE Symposium 1989.
"Acoustical Properties of Clay Bearing Rocks", C. A. Tosaya, 1982.

Primary Examiner—Robert Raevis
Attorney, Agent, or Firm—Guy McClung

[57] ABSTRACT

A microaccumulator for receiving and holding fluid under pressure, and for measuring fluid volume changes in one aspect in very small amounts, and for indicating the amount, the microaccumulator having a body with an interior cavity for receiving the fluid and a piston movably disposed therein which moves in response to a change in fluid amount, the piston having a sensor interconnectible with a monitor and/or system control (e.g. a computer) which can control monitor and/or record changes in the amount of fluid. A triaxial test apparatus for low permeability rock (e.g. shales) using such a microaccumulator. Methods for triaxial tests and for the use of such devices.

13 Claims, 1 Drawing Sheet

U.S. PATENT DOCUMENTS

| | | | |
|---|---|---|---|
| 4,762,003 | 8/1988 | Cioletti | 73/825 |
| 4,791,822 | 12/1988 | Penny | 73/865 |
| 4,799,382 | 1/1989 | Sprunt et al. | 73/153 |
| 4,807,465 | 2/1989 | Botzolakis et al. | 73/78 |
| 4,825,700 | 5/1989 | Vardoulakis et al. | 73/749 |
| 4,827,761 | 5/1989 | Vinegar et al. | 73/38 |
| 4,845,995 | 7/1989 | Kaste et al. | 73/794 |
| 4,848,145 | 7/1989 | Blaschke et al. | 73/153 |
| 4,856,341 | 8/1989 | Vinegar et al. | 73/798 |
| 4,864,846 | 9/1989 | Jones | 73/38 |
| 4,868,751 | 9/1989 | Dogru et al. | 364/422 |
| 4,884,438 | 12/1989 | Jones et al. | 73/153 |
| 4,885,941 | 12/1989 | Vardoulakis et al. | 73/794 |
| 4,922,764 | 5/1990 | Welker | 73/864.62 |
| 4,930,361 | 6/1990 | Nimberger | 73/864.62 |
| 4,955,237 | 9/1990 | Suzuki et al. | 73/784 |
| 4,957,001 | 9/1990 | Powell | 73/716 |
| 4,961,343 | 10/1990 | Boone | 73/152 |

MICROACCUMULATOR FOR MEASUREMENT OF FLUID VOLUME CHANGES UNDER PRESSURE

BACKGROUND OF THE INVENTION

1. Field of the Invention

This invention is directed to microaccumulators for fluid under pressure and, in one aspect, to apparatuses using such devices in quantitative determinations of the strengths and mechanical properties of rock, including low permeability rock such as shale.

2. Description of Related Art

Many prior art pressure generators have a relatively long piston which moves in a small diameter bore. Hence, they have a small bore-diameter-to-piston-stroke length ratio; e.g. 1 to 4; 1 to 7; 1 to 8. Packing around such pistons can be compressed causing leaks. Many larger prior art accumulators require the use of larger linear variable differential transformers (LVDT's; e.g. products of Schaevitz Co. such as HR2000) which are not sensitive to very small volume changes.

In a conventional triaxial test apparatus for rock testing, the sample is deformed by gradually increasing the axial load until the ultimate strength of the specimen is reached at which point it fails; i.e., it will not sustain any further increased axial loading. Water or fluid can drain out of the sample during the test. The pore pressure within the sample is measured by an external pressure gauge or a more accurate pressure transducer via a pore pressure line through the end cap to the rock face. Pore pressure can be applied and controlled externally during a test by pumping water into the sample through the pore pressure line. The loading stage of the conventional test can be relatively fast and typically at high strain rates in the range of $10^{-2}$ to $10^{-4}$ sec$^{-1}$ and sometimes as slow as $10^{-5}$ to $10^{-6}$ sec$^{-1}$ and still achieve pore-pressure equilibrium during the test. Additionally, highly accurate control of the strain rates is not critical and usually not achieved for the typical high strain rates used for higher permeability rocks. An LVDT (linear variable differential transformer) on the load piston has been used to control the strain rate, however more recent applications have used LVDT's on the rock or end caps to obtain more precise control.

The prior art teaches pore pressure measurement for shales in tests with a triaxial end cap design that incorporates an accurate miniaturized pressure transducer into the end cap near the rock face which prevents drainage of the pore water from the rock during the test and which obviates external contact with water from a pore pressure line and thus preserves the original water content of the test specimen throughout the test.

There has long been a need for a microaccumulator for fluid under pressure to receive very small amounts of fluid. There has long been a need for such a device which can be used with triaxial test equipment to sense small amounts of fluid expelled from a test sample. There has long been a need for such a microaccumulator that can be used in triaxial tests of low permeability rocks, e.g. shales.

SUMMARY OF THE PRESENT INVENTION

A microaccumulator device for fluid under pressure, according to the present invention has, in one embodiment, a body made from high strength material (e.g. steel or titanium), the body having an input channel extending from the exterior surface of the body to an interior cavity so that fluid to be accumulated can flow through the channel into the cavity. A piston is movably disposed in the cavity for movement in response to fluid entering the cavity. In one embodiment, a sensor includes a rod of an LVDT secured to the piston and movable with it. The rod extends into an LVDT coil winding. The LVDT is connected to a sensor which senses change in voltage caused by movement of the rod in the coil winding. The sensor has wiring interconnected therewith for connecting the sensor with a control device, e.g. a computer for control, monitoring, and/or recording of data. The coil winding of the LVDT is secured in an LVDT holder which is disposed in the body's cavity adjacent the piston. A pressure control channel permits fluid, e.g. gas or liquid, to be pumped into the cavity to maintain the piston in place or to increase pressure and force fluid back out of the microaccumulator (e.g. into a rock sample being tested with an apparatus including such a microaccumulator). It is preferred that the piston is mounted with an airtight low friction seal (made e.g., plastic or rubber material) and with an alignment bearing. It is preferred that a relatively large diameter piston bore be used with a relatively short drive stroke so that a high stroke-length-to-diameter ratio is achieved. This reduces the possibility of misalignment and reduces wear on seals and bearings as compared to devices with long strokes and/or small diameters. It is also preferred to use an LVDT (e.g. commercially available MHR 100 from Schaevitz Co.) which employs a relatively larger amount of voltage for its length so that the volume change per volt is very low; i.e., its sensitivity is high. Also since the LVDT rod or shaft is guided into a hole in the center of a coil winding lateral movement of the shaft is inhibited and, therefore, displacement errors are reduced; thus allowing voltages to be very reproducible.

In one embodiment, a microaccumulator according to the present invention has a relatively small cavity for receiving fluid, e.g. a cavity with a volume of about 0.25 to about 10 cubic centimeters or less. In one particular device according to this invention for use with triaxial test apparatuses for testing shale core samples, the cavity volume is about 2.6 cubic centimeters. Due to the sensitivity of the LVDT, in preferred embodiments, even minute changes in fluid volume, e.g. as low as between 50 and 0.2 microliters, can be detected.

In one embodiment of a mechanical test apparatus according to the present invention, the test apparatus has an end cap for application to a rock sample, the end cap having a miniature pore pressure transducer in communication with a small diameter pore pressure channel filled with a fluid and a secondary channel communicating with the pore pressure channel and with a microaccumulator according to the present invention.

It is, therefore, an object of the present invention to provide new, useful, efficient, unique, and non-obvious microaccumulators for fluids under pressure.

Another object of the present invention is the provision of such accumulators which can be used effectively with triaxial test apparatuses, and particularly with apparatuses used in testing low permeability rock, such as shales.

Yet another object of the present invention is the provision of such devices which can effectively and accurately indicate relatively small fluid volume changes.

A further object of the present invention is the provision of such a microaccumulator with a relatively large piston-stroke-length-to-piston-bore-diameter ratio.

An additional object of the present invention is the provision of such a device in which sensing errors are minimized and settings are reproducible.

Appended hereto and included herein fully for all purposes are copies of the following patent applications filed on even date with this application, all applications co-owned by the same assignee:

"Methods And Apparatuses For Measurement Of The Strengths, Pore Pressures, And Mechanical Properties Of Low Permeability Geologic Materials," naming Mr. Ronald P. Steiger as inventor.

"Methods For Determining In Situ Shale Strengths, Elastic Properties, Pore Pressures, Formation Stresses And Drilling Fluid Parameters," naming Messrs. Ronald P. Steiger and Peter K. Leung as co-inventors.

"Test Apparatuses And Methods For Adjusting A Material's Fluid Content And Effective Stresses," naming Messrs. Ronald P. Steiger and Peter K. Leung as co-inventors.

"Apparatuses and Methods For Measuring Ultrasonic Velocities In Materials," naming Messrs. Ronald P. Steiger an Peter K. Leung as co-inventors.

The present invention addresses the unrecognized long-felt need for an accurate microaccumulator and provides a satisfactory meeting of this need in its various possible embodiments. To one of skill in this art who has the benefits of this invention's teachings and disclosures, other and further objects and advantages will be clear, as well as others inherent therein, from the following description of presently-preferred embodiments, given for the purpose of disclosure, when taken in conjunction with the accompanying drawings. Although these descriptions are detailed to insure adequacy and aid understanding, this is not intended to prejudice that purpose of a patent which is to claim an invention no matter how others may later disguise it by variations in form or additions or further improvements.

DESCRIPTION OF THE DRAWINGS

So that the manner in which the above-recited features, advantages and objects of the invention, as well as others which will become clear, are attained and can be understood in detail, more particular description of the invention briefly summarized above may be had by reference to certain embodiments thereof which are illustrated in the appended drawings, which drawings form a part of this specification. It is to be noted, however, that the appended drawings illustrate preferred embodiments of the invention and are therefore not to be considered limiting of its scope, for the invention may admit to other equally effective equivalent embodiments.

DESCRIPTION OF EMBODIMENTS PREFERRED AT THE TIME OF FILING FOR THIS PATENT

Figure 1:
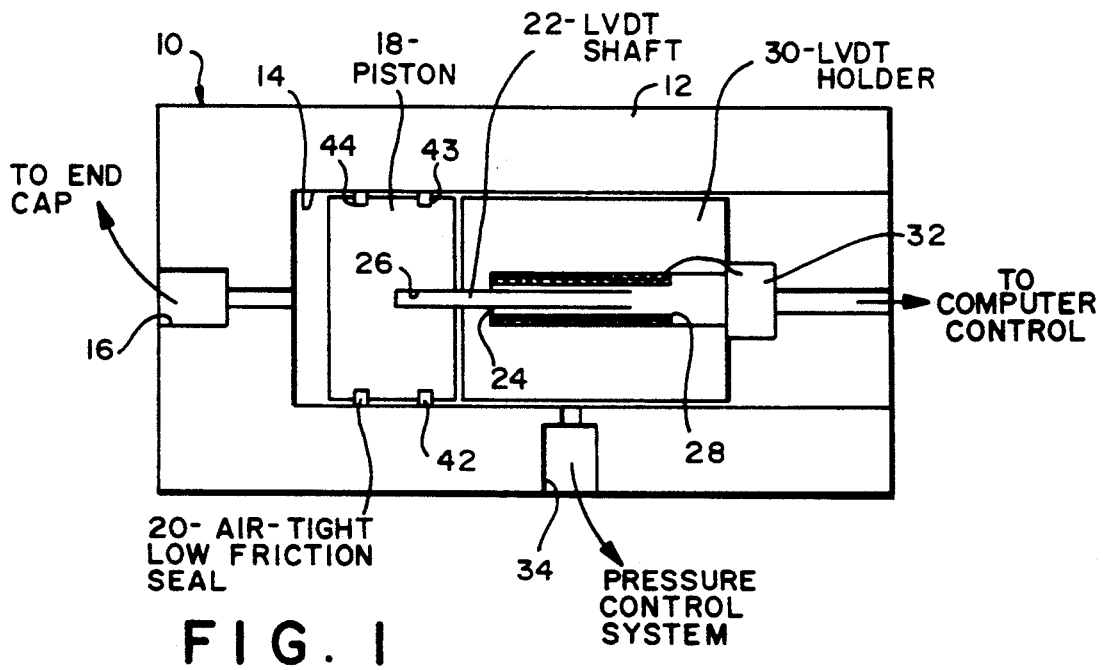
FIG. 1 is a cross-sectional schematic view (to scale) of a microaccumulator according to the present invention.

Referring now to FIG. 1, a microaccumulator 10 according to the present invention has a body 12 with an interior cavity 14. A fluid channel 16 permits fluid to flow into the cavity 14. A piston 18 is movably disposed within the cavity 14 and an air-tight low-friction seal 20 in a recess 44 (preferably rubber or plastic with reinforcing rings, not shown) prevents fluid from flowing beyond the piston between the piston and the cavity's inner wall. Low friction Polypack seals from Polypack Co. have been used. A bearing 42, preferably made from Nylon (TM) in a recess 43 helps maintain alignment of the piston 18 in the body.

A shaft 22 of an LVDT 24 is secured to the piston 18 in a recess 26 in the piston. As the piston 18 moves, the shaft 22 moves in a coil winding 28 of the LVDT 24. An LVDT holder 30 supports the coil winding 28 and encloses it. A sensor 32 is interconnected between the LVDT 24 and a control device such as a computer 40 via wiring 41. The sensor has wiring interconnected therewith for connecting the sensor with the control device, e.g. a computer for control, monitoring, and/or recording of data. The sensor senses changes in voltage (indicating volume change) caused by movement of the shaft 22 of the LVTT 24 in the coil winding 28.

A pressure control channel 34 permits fluid, e.g. gas (e.g. nitrogen) to enter the cavity 14 behind the piston 18 to maintain the piston in position or to provide pressure from the microaccumulator.

It is preferred that the accumulator body 12 and the piston 18, be made from high strength material such as titanium or steel. It is preferred that the LVDT holder 30 be made from aluminum. One LVDT usable with the device 10 is a conventional LVDT which is commercially available, the MHR 100 of Schaevitz Co. The body 12 is, preferably, designed for operation with fluids under pressure up to 10000 p.s.i. plus a 50% safety factor; e.g. 15000 p.s.i. Thus, the effect of pressures encountered on the body is small.

Figure 2:
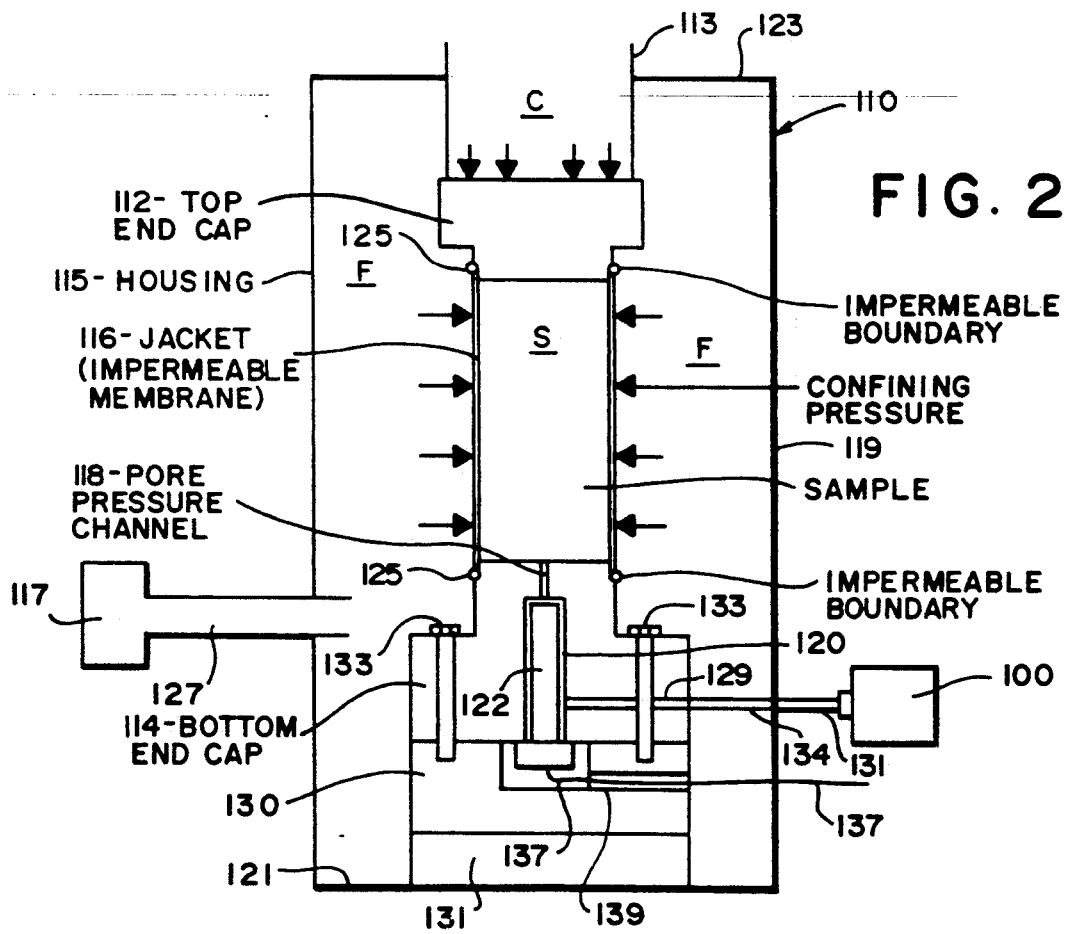
FIG. 2 presents schematically (not to scale) a triaxial test apparatus with a microaccumulator according to this invention.

As shown schematically in FIG. 2, a triaxial test apparatus 110 according to the present invention has a housing 115 preferably made from titanium or high strength steel with a side wall 119, (preferably generally cylindrical) a bottom plate 121, and a top plate 123. A sample mounting apparatus has a top end cap 112 and a bottom end cap 114 that is bolted with bolts 133 to a bottom base 130 that rests on a load cell 131 which itself is on the bottom plate 121. A microaccumulator 100 (like the accumulator 10 in FIG. 1) is interconnected, via a channel 129 and stiff lines 134 and 181, with a fluid chamber 120 in the bottom end cap 114. A valve 132 controls flow through the stiff line 181. A recess 135 in the base 130 accommodates part of the transducer 122 and wiring 137 from the transducer exits from a sealed lead through 139.

A sample S, placed between the end caps, is sheathed with an impermeable jacket 116. The end caps are made from high strength materials, (e.g. titanium or hardened steel) and the boundaries between the end caps and the jacketed sample are impermeable. The jacket extends slightly beyond the sample on the end caps and wire ropes 125 secure the ends of the jacket about the end caps. The end caps have flat, polished smooth surfaces for contacting the sample with diameters closely matched to that of the sample; i.e. it is preferred that they be within 0.005 inches of each other. Also, it is preferred that samples' ends' flatness be within 0.001 inch per inch of diameter. For example, for an upright sample, over a dimension of one inch of the sample's top surface the surface height does not vary more than 0.001 of an inch, no matter where along that inch of the surface a height measurement is taken. This minimizes void space between end cap and sample; provides uniform loading of the sample; and minimizes unwanted end effects.

The bottom end cap 114 has a pore pressure channel 118 which communicates with the fluid chamber or port 120. A pore pressure transducer 122 is disposed in the fluid chamber 120. A non-wetting inert fluid (e.g. mercury which is not very compressible) immiscible in the fluid to be expelled from the sample, e.g. water, is placed in the pore pressure channel 118, in the fluid chamber 120 in the line 129, the line 181, and in the microaccumulator itself. Preferably, the pore pressure channel 118, the fluid chamber 120, the channel 129, the line 134, the line 181, and space in the microaccumulator 100 are vacuum evacuated prior to the introduction of mercury so that no air is trapped therein which could adversely affect test results.

Preferably, the pore pressure transducer 122 is an accurate miniature strain-gauge type pressure transducer interfaced with a digital data acquisition system 140 via wiring 137. In one embodiment, it is preferred that the microaccumulator be able to sense volume changes as low as about 50 microliters and preferably as low as about 0.2 microliters. In general, it is preferred that a microaccumulator according to the present invention be able to measure amounts of fluid expelled from a sample such that the ratio of fluid expelled from a sample to total fluid in a sample is between 12.5 to 0.05 (microliters of expelled fluid/cubic centimeters of fluid in sample). For example, if the sample initially has about 1 cubic centimeter of fluid in it, it is preferred that it be possible to measure an amount of fluid expelled from the sample ranging from 12.5 microliters to 0.05 microliters.

In one embodiment of a microaccumulator according to the present invention, the piston stroke is about 0.2 inches and its bore is about 1 inch in diameter. This provides a relatively high bore-diameter stroke-length ratio (about 5:1) It is preferred that this ratio be at least about 1 to 3 and no greater than about 10 to 1. With larger diameters and shorter strokes there is less friction and misalignment of the piston is reduced, as well as reducing seal wear. In this embodiment, the interior cavity of the body has a volume for receiving fluid of about 2.6 cubic centimeters. It is preferred that the interior volume of the microaccumulator be between about 0.25 cubic centimeters and about 10 cubic centimeters.

It is preferred that the ratio of the interior volume of the microaccumulator that can receive fluid to the volume of sample fluid in a sample when triaxial testing of it begins is between about 0.0625 to about 2.5.

A hydraulic fluid F pumped by a fluid pumping and controlling system 117 exterior to the housing 115 and communicating with the housing's interior via line 127 surrounds the sample S and the top end cap 112 providing a desired confining pressure for the sample S and pressure on the top end cap 112.

In a typical operation of the apparatus 110, the microaccumulator is set by applying desired back gas pressure through the pressure control channel 34 at a pressure level, e.g. 2000 p.s.i., and the confining pressure on the sample is adjusted to 2500 p.s.i. The sample's pore pressure is allowed to equilibrate with the confining pressure, during which equilibration fluid is expelled from the sample into the pore pressure channel of the end cap compressing the mercury in the pore pressure channel. This change produces a change in volume in the microaccumulator and causes the LVDT shaft to move in the coil winding, sending a signal to a monitor/control system e.g. a computer for control, monitoring, and/or recording of data. Once this step is completed, another step can be commenced, e.g. setting the confining pressure higher than 2500 p.s.i. and further draining the sample. Alternatively, pressure control fluid can be pumped into the pressure control port of the microaccumulator to force fluid back into the sample at which point, after equilibration, measurements of volume change by the LVDT can be noted.

In conclusion, therefore, it is seen that the present invention and the embodiments disclosed herein are well adapted to carry out the objectives and obtain the ends set forth at the outset. Certain changes can be made in the method and apparatus without departing from the spirit and the scope of this invention. It is realized that changes are possible and it is further intended that each element o step recited in any of the following claims is to be understood as referring to all equivalent elements or steps for accomplishing substantially the same results in substantially the same or equivalent manner. It is intended to cover the invention broadly in whatever form its principles may be utilized. The present invention is, therefore, well adapted to carry out the objects and obtain the ends and advantages mentioned, as well as others inherent therein.

What is claimed is:

1. A microaccumulator for receiving and holding fluid under pressure and for indicating changes in the volume of the fluid, the microaccumulator comprising:

a body for an interior cavity, a piston movably and sealingly disposed in a bore in the cavity, a fluid channel extending from an exterior surface of the body to the interior cavity through which fluid to be received and held may pass into a first portion of the interior cavity on a first side of the piston, wherein the fluid received into the interior cavity is proportional to an amount of sample fluid expelled from a rock sample during a triaxial test of the sample, the sample expelling the sample fluid into a test channel of a triaxial test apparatus disposed adjacent an end of the sample, the test channel in fluid communication with the fluid channel of the microaccumulator, and for each cubic centimeter of sample fluid in the sample prior to testing between 12.5 to 0.05 microliters are expelled from the sample and measured during testing, indicator means in the interior cavity for indicating the amount of fluid in the interior cavity, the indicator means comprising a linear variable differential transformer with a shaft movable in a coil winding, the shaft connected to the piston so that movement of the piston moves the shaft in the coil to produce a signal indicative a change in volume of fluid in the first portion of the interior cavity, and a pressure control channel extending from an exterior surface of the body to the interior of the cavity through which pressure control fluid may pass into a second portion of the cavity on a second side of the piston opposite the first side of the piston.

2. A microaccumulator for receiving and holding fluid under pressure and for indicating changes int eh volume of the fluid, the microaccumulator comprising:
 a body for an interior cavity,
 a piston movably and sealingly disposed in a bore in the cavity,
 a fluid channel extending from an exterior surface of the body to the interior cavity through fluid to be received and held may pass into a first portion of the interior cavity on a first side of the piston, wherein the fluid received into the interior cavity is proportional to an amount of sample fluid expelled from a rock sample during a triaxial test of the sample, the sample expelling sample fluid into a test channel of a triaxial test apparatus disposed adjacent an end of the sample, the test channel in fluid communication with the fluid channel of the microaccumulator, and the ratio of a volume of the interior cavity on the first side of the piston to a total volume of sample fluid in the sample when testing begins being between about 0.0625 and about 2.5,
 indicator means in the interior cavity for indicating the amount of fluid in the interior cavity,
 the indicator means comprising a linear variable differential transformer with a shaft movable in a coil winding, the shaft connected to the piston so that movement of the piston moves the shaft in the coil to produce a signal indicative a change in volume of fluid in the first portion of the interior cavity, and
 a pressure control channel extending from an exterior surface of the body to the interior of the cavity through which pressure control fluid may pass into a second portion of the cavity on a second side of the piston opposite the first side of the piston.

3. A triaxial test device for testing a rock sample, the device comprising
 a housing fillable with confining fluid for providing confining pressure on the sample, the housing having an inlet for introduction therein and removal therefrom of the confining fluid,
 a rock sample mounting apparatus including,
 a top end cap for contacting disposition above the sample,
 a bottom end cap for contactingly supporting the sample from beneath it, the bottom end cap having,
 a cap body,
 a pore pressure channel in the cap body in fluid communication with a bottom end of the sample and into which sample fluid expelled from the rock sample during testing flows,
 a pore pressure port in the cap body in fluid communication with the pore pressure channel, a pore pressure fluid in the pore pressure channel and in the pore pressure port, the expelled sample fluid contacting the pore pressure fluid,
 a pore pressure transducer disposed in the pore pressure port for reacting to and indicating changes in pressure of the sample fluid, the pore pressure transducer collectible to a monitor system,
 a microaccumulator in fluid communication with the pore pressure port for receiving fluid therefrom, holding it, and indicating its volume, the microaccumulator comprising
 a first body having an interior cavity,
 a piston movably and sealingly disposed in a bore in the cavity,
 a fluid channel extending from an exterior surface of the first body to the interior cavity through which fluid to be received and held may pass into a first portion of the interior cavity on a first side of the piston,
 indicator means in the interior cavity for indicating the amount of fluid in the interior cavity, and
 a pressure control channel extending from an exterior surface of the first body to the interior of the cavity through which pressure control fluid may pass into a second portion of the cavity on a second side of the piston opposite the first side of the piston.

4. The triaxial test device of claim 3 including also a flexible impermeable sheath around the sample preventing the confining fluid from directly contacting the sample.

5. The triaxial test device of claim 3 wherein the rock sample is a low permeability rock.

6. A triaxial test device for testing a rock sample, the device comprising
 a housing fillable with confining fluid for providing confining pressure on the sample, the housing having an inlet for introduction therein and removal therefrom of the confining fluid,
 a rock sample mounting apparatus including,
 a top end cap for contacting disposition above the sample,
 a bottom end cap for contactingly supporting the sample from beneath it, the bottom end cap having,
 a cap body,
 a pore pressure channel in the cap body in fluid communication with a bottom end of the sample and into which flows sample fluid expelled from the rock sample during testing,
 a pore pressure port in the cap body in fluid communication with the pore pressure channel, the pore pressure channel and pore pressure port filled with pore pressure fluid, the sample fluid expelled contacting the pore pressure fluid,
 a pore pressure transducer disposed in the pore pressure port for reacting to and indicating changes in pressure of the sample fluid, the pore pressure transducer and collectible to a monitor system, and
 a microaccumulator in fluid communication with the pore pressure port for receiving fluid therefrom, holding it, and indicating its volume, the microaccumulator comprising
 a first body having an interior cavity,
 a piston movably and sealingly disposed in a bore in the cavity,
 a fluid channel extending from an exterior surface of the first body to the interior cavity through which fluid to be received and held may pass into a first portion of the interior cavity on a first side of the piston,
 indicator means in the interior cavity for indicating the amount of fluid in the interior cavity, the indicator means comprising a linear variable differential transformer including a holder, a coil winding within the holder, collectible to a control system exterior to the microaccumulator, a shaft partially movable within the coil and having an end secured to the piston, the shaft moving as the piston moves, and
 a pressure control channel extending from an exterior surface of the first body to the interior of the cavity through which pressure control fluid may pass into a second portion of the cavity on a second side of the piston opposite the first side of the piston.

7. A triaxial test device for a testing rock sample, the device comprising
   a housing fillable with confining fluid for providing confining pressure on the sample, the housing having an inlet for introduction therein and removal therefrom of the confining fluid,
   a rock sample mounting apparatus including,
   a top end cap for contacting disposition above the sample,
   a bottom end cap for contactingly supporting the sample from beneath it, the bottom end cap having,
   a cap body,
   a pore pressure channel in the cap body in fluid communication with a bottom end of the sample and into which flows sample fluid expelled from the rock sample during testing,
   a pore pressure port in the cap body in fluid communication with the pore pressure channel, a pore pressure fluid in the pore pressure channel and in the pore pressure port, the expelled sample fluid contacting the pore pressure fluid,
   a pore pressure transducer disposed in the pore pressure port for reacting to and indicting changes in pressure of the sample fluid, the pore pressure transducer collectible to a monitor system, and
   a microaccumulator in fluid communication with the pore pressure port for receiving fluid therefrom and holding it, the microaccumulator comprising
   a first body having an interior cavity into which fluid may flow, the interior cavity having a volume for such fluid between about 0.25 cubic centimeters to about 10 cubic centimeters,
   a piston movably and sealingly disposed in a bore in the cavity,
   a fluid channel extending from an exterior surface of the first body to the interior cavity through which fluid to be received and held may pass into a first portion of the interior cavity on a first side of the piston,
   indicator means in the interior cavity for indicating the amount of fluid in the interior cavity, indicator means comprising a linear variable differential transformer including a holder, a coil winding within the holder collectible to a control system exterior to the microaccumulator, a shaft movable within the coil and having an end secured to the piston, the shaft moving as the piston moves, and
   a pressure control channel extending from an exterior surface of the first body to the interior of the cavity through which pressure control fluid may pass into a second portion of the cavity on a second side of the piston opposite the first side of the piston.

8. A method for sensing and indicating the change in the amount of sample fluid expelled from a rock sample during a triaxial test of the sample, the method comprising
   flowing sample fluid expelled from the sample into a channel in an end cap of a triaxial test mounting apparatus, the channel in fluid communication with an inner cavity of a body of a microaccumulator, the flowing sample fluid contacting a fluid in the channel and in the body thereby moving a piston sealingly and movably disposed in a bore in the cavity, the piston moving as the amount of fluid changes,
   sensing the amount of movement of the piston with sensor means within the cavity for sensing the movement, the sensor means providing a signal indicative of piston position, the signal transmittable from the microaccumulator to a control system which translates the signal to indicate volume, and
   providing pressure control fluid on a second side of the piston opposite from a first side of the piston in contact with the sample fluid.

9. The method of claim 8 wherein the sensing is accomplished by a linear variable differential transformer.

10. The method of claim 8 wherein the microaccumulator can hold between about 0.25 cubic centimeters to about 10 cubic centimeters of fluid and the sensor means can sense a volume change as low as 50 microliters.

11. The method of claim 8 wherein the pressure control fluid is a gas and the piston is sealed against the cavity with a gas-tight seal.

12. The method of claim 8 wherein the pressure control fluid is nitrogen.

13. A method for sending and indicating the change in the amount of sample fluid expelled from a rock sample, during a triaxial test of the sample, the method comprising
   flowing sample fluid expelled from the sample into a channel in an end cap of a triaxial test mounting apparatus, the channel in fluid communication with an inner cavity of a body of a microaccumulator, the flowing sample fluid contacting a fluid in the body channel and in the body thereby moving a piston sealingly and movably disposed in a bore in the cavity, the piston moving as the amount of fluid changes, the inner cavity having a volume for receiving to about 2.6 cubic centimeters of such fluid,
   sensing with a sensor the amount of movement of the piston within the cavity, the sensor providing a signal indicative of fluid amount in the cavity, the sensor including a linear variable differential transformer, the signal transmittable from the accumulator to a control system,
   providing pressure control fluid on a second side of the piston opposite from a first side of the piston in contact with the sample fluid, and
   the pressure control fluid being nitrogen gas and the piston sealed against the inner cavity with a gas-tight seal.

* * * * *